NEW AND DISTINCT VARIETY OF BLUEGRASS PLANT

Filed Sept. 17, 1970 2 Sheets-Sheet 1

NEW AND DISTINCT VARIETY OF BLUEGRASS PLANT

Filed Sept. 17, 1970

United States Patent Office

Plant Pat. 3,150
Patented May 2, 1972

3,150

NEW AND DISTINCT VARIETY OF BLUEGRASS PLANT

Gerard William Pepin, North Brunswick, and Cyril Reed Funk, Jr., Milltown, N.J., assignors to Rutgers University, New Brunswick, N.J.

Filed Sept. 17, 1970, Ser. No. 73,270
Int. Cl. A01h *5/00*
U.S. Cl. Plt.—88 1 Claim

ABSTRACT OF THE DISCLOSURE

A Kentucky bluegrass plant which exhibits excellent seed producing properties and a rich dark green color. The turf is quite leafy and of high quality, with good density and vigor. The plant has good resistance to common grass diseases, particularly stripe smut, leaf spot and leaf rust.

The present invention relates to a new and distinct variety of Kentucky bluegrass plant, the novel characteristics of which reside particularly in its excellent seed producing properties, a high quality turf, and a rich, dark green color.

The new variety was originated by us by crossing an unpatented selection identified in our breeding records as "Bellvue" with another unpatented selection identified as "Belturf," "Bellvue" being the seed parent and "Belturf" being the pollen parent. As a result of this breeding, we have produced and asexually propagated by rhizomes, tillers and desseminules a new and improved Kentucky bluegrass variety which is distinguished from its parents, as well as from all other varieties of which we are aware. The plants of the new variety were labeled "NJE P–69" Kentucky bluegrass.

NJE P–69 Kentucky blueglass (*Poa pratensis*) is perennial with a leafy growth habit tolerant of moderately close mowing. The plant is a good seed producer and is resistant to such grass diseases as stripe smut, leaf spot and crown rot, and leaf rust.

In comparison with its seed parent, Bellvue, the new variety has finer leaves, a darker green color, maintains a more leafy turf during late spring and has higher turf performance ratings.

In comparison with its pollen parent, Belturf, the new variety has more panicles per plant, better resistance to leaf spot and crown rot disease incited by the fungus *Helminthosporium vagans,* and better turf performance ratings.

A primary object of the invention is to provide a new and distinct variety of bluegrass plant having the desirable characteristics referred to above and to be described in detail below.

Other objects and advantages of the invention will become more fully apparent from the following detailed description when taken in conjunction with the accompanying illustrations, in which.

Figure 1:
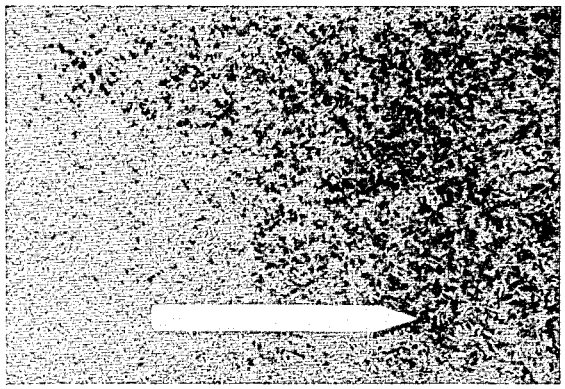
FIG. 1 shows a typical turf plot of the new variety.
Figure 2:
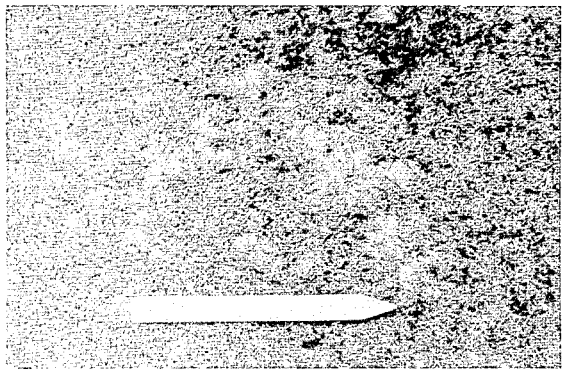
FIG. 2 shows a turf plot of Delta Kentucky bluegrass (unpatented), illustrating its contrast with respect to the a new variety of FIG. 1.
Figure 3:
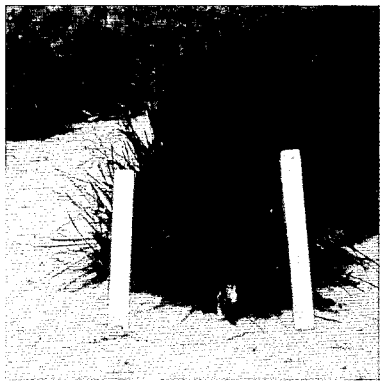
FIG. 3 shows a plant of the new variety approximately one week before the flowering stage.
Figure 4:
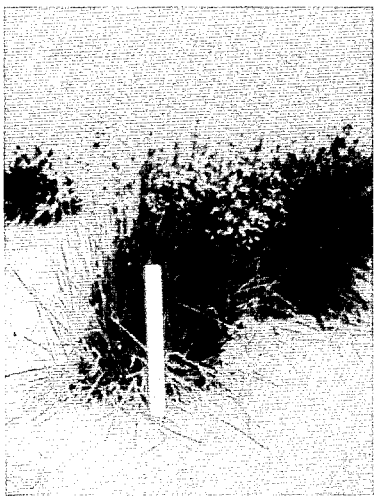
FIG. 4 shows a plant of the new variety under different lighting conditions after the completion of the flowering stage.
Figure 5:
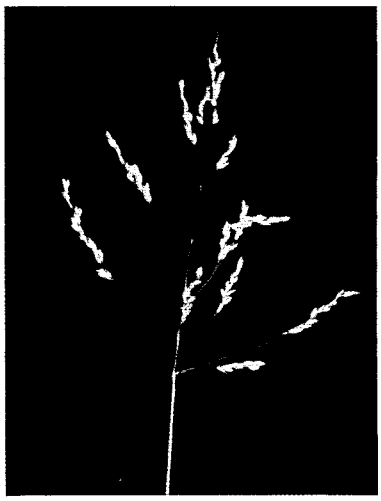
FIG. 5 shows a panicle of the new variety.
Figure 6:
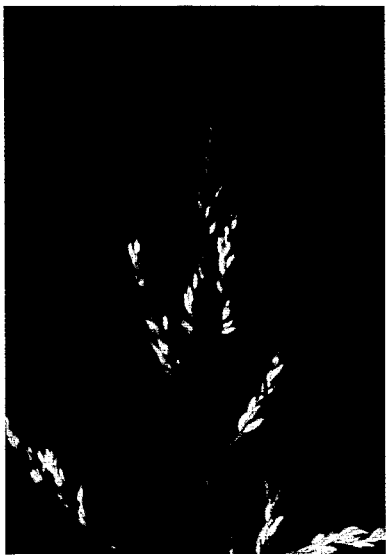
FIG. 6 shows a cluster of spikelets of the new variety.

NJE P–69 exhibits at least the following unique combination of characteristics:

(1) Good resistance to the leaf spot and crown rot disease incited by the fungus *Helminthosporium vagans*;

(2) Good resistance to the stripe smut disease incited by the fungus *Ustilago striiformis*;

(3) Good resistance to the leaf rust disease caused by the fungus *Puccinia poae-nemoralis*;

(4) A leafy turf-type growth habit tolerant of moderately close mowing;

(5) Good rhizome and tiller development under turf maintenance, producing a turf of excellent density and moderate horizontal spreading ability;

(6) An attractive, rich, deep, dark green color which is maintained throughout the growing season;

(7) Moderate leaf texture;

(8) Good turf performance.

PLANT DESCRIPTION

The plants of the new variety which are described herein were grown in New Jersey. The culms of the variety are rather erect but are usually bent at the lower nodes. The culms are tufted, average 73 cm. in height when undisturbed by clipping, are moderately stout, cylindrical, usually with four nodes, and smooth. Leaves are dark green; sheaths smooth with those on vegetative shoots compressed and keeled, hairless; ligules membraneous, and very short on vegetative tillers but about 1 to 1.5 mm. long on reproductive tillers; edge of collar fringed with fine hairs; blades 3 to 4 mm. wide, initially folded but then opening out with a boat-shaped apex; the flag leaf averages 52.0 mm. in length. Panicles pyramidal open, with main axis moderately erect and averaging 104 mm. long; lower branches mostly in clusters of 2 to 5 (average 3.7). Spikelets ovate, compressed 3.7 to 5.5 mm. long (average 4.6 mm.), 3 to 5 flowered (average 3.7) breaking up at maturity beneath each lemma. Glumes persistent, pointed, unequal, rough on the keels, lower mostly one-nerved, ovate, averaging 2.6 mm. long; upper three-nerved, ovate to elliptic averaging 2.9 mm. long; lemmas overlapping, five-nerved, oblong or ovate in side view, pointed tip, hair on the keel and nerves to the middle, long fine crinkled hair at the base and on the lower margin. Paleas about as long as the lemmas with 2 rough keels. Grain tightly enclosed in the lemma and palea.

Since soil and climatic factors influence morphological characteristics to some degree these characters may vary slightly under different conditions. The morphological characteristics of NJE P–69 and other bluegrasses measured in 1970 at Adelphia, N.J., are shown in Table 1.

TABLE 1.—MORPHOLOGICAL COMPARISON OF NJE P-69 AND OTHER BLUEGRASS VARIETIES

| Variety | Plant height, cm. | Plant diameter, cm. | Leaf blade width, mm. | Hairs on edge of collar [1] | Hairs on ligule [1] | Flag leaf length, mm. | No. of panicles per plant | Panicle color [2] | Panicle erect or nodding [3] | Number of branches at lowest panicle node | Panicle length, mm. |
|---|---|---|---|---|---|---|---|---|---|---|---|
| NJE P-69 | 73 | 34 | 3.7 | 3.5 | 2.7 | 52 | 272 | 2.0 | 1.8 | 3.7 | 104 |
| Delta | 73 | 17 | 2.6 | 1.5 | 0.0 | 67 | 196 | 2.0 | 1.0 | 4.8 | 100 |
| Geary | 80 | 24 | 2.9 | 2.0 | 0.0 | 80 | 177 | 3.0 | 3.0 | 4.0 | 134 |
| Newport | 79 | 30 | 4.8 | 3.7 | 3.7 | 77 | 246 | 2.5 | 2.0 | 4.3 | 105 |
| Palouse | 79 | 24 | 3.0 | 1.0 | 0.0 | 93 | 151 | 3.0 | 3.5 | 4.4 | 92 |
| Anheuser Dwarf | 67 | 30 | 5.1 | 2.5 | 2.0 | 51 | 109 | 3.0 | 2.5 | 3.4 | 96 |
| Belturf | 70 | 35 | 3.0 | 2.0 | 1.0 | 58 | 201 | 2.0 | 2.0 | 4.0 | 104 |
| Fylking (Patent 2,887) | 60 | 34 | 4.0 | 1.5 | 1.5 | 68 | 164 | 3.5 | 5.0 | 4.9 | 118 |
| Merion | 70 | 24 | 4.3 | 3.5 | 0.5 | 69 | 280 | 2.0 | 1.5 | 3.5 | 102 |
| Pennstar | 59 | 34 | 3.7 | 2.2 | 1.0 | 66 | 132 | 3.5 | 4.0 | 4.5 | 106 |

[1] Scale: 0=No hairs; 5=most hairs [2] Scale: 0=Green; 5=purple. [3] Scale: 1=Erect; 5=nodding.

TURF CHARACTERISTICS

The new variety has exhibited consistently high turf performance ratings. The turf has a leafy quality which is maintained during late spring, and exhibits good density and vigor and an extremely attractive color.

Overall turf performance and color ratings for NJE P–69 and other bluegrasses at New Brunswick, N.J., are listed in Table 2.

TABLE 2.—TURF PERFORMANCE AND COLOR RATINGS OF NJE P-69 AND OTHER BLUEGRASS VARIETIES

| Variety | Turf performance (9=best) | | | | | | Color (9=most attractive March 1970 |
|---|---|---|---|---|---|---|---|
| | 1966 | 1967 | 1968 | 1969 | 1970 | Average | |
| NJE P-69 | 6.8 | 7.3 | 8.2 | 7.3 | 6.9 | *7.3 | 6.0 |
| Merion | 6.3 | 6.1 | 6.8 | 4.9 | 4.1 | 5.6 | 3.0 |
| Delta | 4.5 | 4.2 | 5.2 | 4.9 | 4.5 | 4.7 | 4.0 |
| Pennstar | 6.9 | 6.8 | 7.9 | 7.1 | 7.2 | *7.2 | 3.0 |
| Fylking | 6.9 | 6.8 | 8.0 | 7.6 | 7.2 | *7.3 | 3.0 |
| Windsor | 5.0 | 5.0 | 6.4 | 5.4 | 4.3 | 5.2 | 3.0 |
| Bellvue | 6.4 | 6.7 | 6.9 | 5.9 | 5.7 | 6.3 | |
| Belturf | 6.2 | 5.9 | 7.4 | 7.0 | 6.2 | 6.5 | 3.0 |

NOTE.—Values marked (*) do not differ significantly at the 5% probability level.

DISEASE RESISTANCE

A comparison of NJE P–69 and other bluegrass varieties for resistance to stripe smut caused by the fungus *Ustilago striiformis,* leaf spot caused by the fungus *Helminthosporium vagans,* and leaf rust caused by the fungus *Puccinia poae-nemoralis* is given in the following table:

TABLE 3.—RELATIVE DISEASE RESISTANCE COMPARISON FOR NJE P-69 AND OTHER BLUEGRASSES AT NEW BRUNSWICK, N.J.

| Variety | Stripe smut infected tillers per square foot | Percent leaf spot damage | Leaf rust disease[1] |
|---|---|---|---|
| NJE P-69 | *3 | 7 | *1.3 |
| Merion | 228 | 5 | 3.5 |
| Delta | 11 | 80 | |
| Pennstar | *0 | 6 | *1.5 |
| Fylking | *0 | 6 | *1.5 |
| Windsor | 41 | 25 | |
| Bellvue | 11 | | |
| Belturf | *2 | 20 | |
| Newport | | | 3.5 |

[1] Scale: 0=no rust; 9=disease most severe.

NOTE.—Values marked (*) do not differ significantly at the 5% probability level.

It is apparent from the foregoing table that NJE P–69 exhibits good resistance to stripe smut, leaf spot and leaf rust diseases.

REPRODUCTION AND PROPAGATION

Asexual reproduction of the new variety by tillers and rhizomes and by disseminules (modified caryopses produced by agamospermy) has consistently produced progeny plants indistinguishable from the mother plant.

The new variety has demonstrated good seed producing properties. In addition, it exhibits a rich attractive, dark green color, very good turf performance, and good rhizome and tiller production.

What is claimed is:

1. A new and distinct variety of Kentucky bluegrass plant, substantially as herein shown and described, characterized particularly by very good turf performance, moderate texture, a rich, dark green color, good rhizome and tiller production, and a leafy growth habit.

No references cited.

ROBERT E. BAGWILL, Primary Examiner